United States Patent
Svanberg et al.

(10) Patent No.: US 8,150,114 B2
(45) Date of Patent: Apr. 3, 2012

(54) METHOD FOR ENSURING QUALITY OF A SAMPLE CARRIER

(75) Inventors: Kenth Svanberg, Laholm (SE); Fredrik Jönsson, Mellbystrand (SE)

(73) Assignee: Hemocue AB, Ängelholm (SE)

(*) Notice: Subject to any disclaimer, the term of this patent is extended or adjusted under 35 U.S.C. 154(b) by 882 days.

(21) Appl. No.: 12/087,409

(22) PCT Filed: Jan. 24, 2007

(86) PCT No.: PCT/SE2007/000061
§ 371 (c)(1),
(2), (4) Date: Sep. 3, 2008

(87) PCT Pub. No.: WO2007/086794
PCT Pub. Date: Aug. 2, 2007

(65) Prior Publication Data
US 2008/0317326 A1    Dec. 25, 2008

(30) Foreign Application Priority Data

Jan. 25, 2006 (SE) ....................................... 0600157

(51) Int. Cl.
*G06K 9/00* (2006.01)
(52) U.S. Cl. .......................... 382/128; 382/133; 382/134
(58) Field of Classification Search ........... 382/128–134
See application file for complete search history.

(56) References Cited

U.S. PATENT DOCUMENTS

| 5,841,907 A | 11/1998 | Javidi et al. |
| 5,985,215 A | 11/1999 | Sakazume et al. |
| 2002/0009395 A1* | 1/2002 | Hirono et al. .................. 422/67 |
| 2004/0086173 A1 | 5/2004 | Itoh |
| 2004/0249835 A1* | 12/2004 | Langeveld et al. ............ 707/100 |

FOREIGN PATENT DOCUMENTS

| FR | 2703156 A1 | 3/1993 |
| JP | 10096734 (A) | 4/1998 |
| JP | 2001033462 (A) | 2/2001 |
| JP | 2001108690 (A) | 4/2001 |
| JP | 2001165936 (A) | 6/2001 |
| JP | 2002040034 (A) | 2/2002 |

OTHER PUBLICATIONS

English Translation of Official Action from Japanese Patent Application No. 2008-551224, mailed Jan. 21, 2011.
IBM TDB—G. Ashcraft et al, "Identifying Laser Engraving for Logo and Quality", ip.com, IPCOM00003648OD, Oct. 1m 1989, TDB 10-89 p. 77-79,Jan. 29, 2005, 3 pages.
Translation of Official Action dated Sep. 21, 2010 in Japanese Patent Appln. No. 2008-551224.

* cited by examiner

*Primary Examiner* — Wesley Tucker
(74) *Attorney, Agent, or Firm* — Buchanan Ingersoll & Rooney PC

(57) ABSTRACT

A method is provided for ensuring the quality of a sample carrier in connection with performing an analysis of a sample in the sample carrier in an analysis instrument for in vitro diagnosis, wherein the sample carrier is provided with a symbol for confirming the compatibility of the sample carrier with the analysis instrument. The method comprises bringing the sample carrier to an imaging position in the analysis instrument, acquiring an image of the sample carrier, and analyzing the acquired image to detect the presence of a symbol for identifying the genuineness of the sample carrier. Where the sample carrier is identified as genuine, the sample carrier is approved for use in the analysis instrument and the analysis instrument is enabled to perform an analysis of the sample in the sample carrier. The analysis comprises irradiating the sample by transmitting electromagnetic radiation through the sample carrier.

15 Claims, 2 Drawing Sheets

METHOD FOR ENSURING QUALITY OF A SAMPLE CARRIER

TECHNICAL FIELD

The present invention relates to a method for ensuring the genuineness of a sample carrier in connection with use of the sample carrier in an analysis instrument for in vitro diagnosis.

BACKGROUND OF THE INVENTION

An instrument for in vitro diagnosis provides a possibility to analyse a sample taken from a patient in order to make a diagnosis of a health condition of the patient. It is important that the results of the analysis are accurate and within the specified error margins, since an inaccurate analysis result may lead to incorrect diagnosis, which may have hazardous effects.

The Directive 98/79/EC on in vitro diagnostic medical devices was recently introduced in order to protect the health and environment of patients and third parties in connection with use of such devices. The devices falling under the In Vitro Diagnostic Directive must be designed and manufactured in such a way that, when used under the conditions and for the purposes intended, they will not compromise, directly or indirectly, the clinical condition or the safety of the patients. They must achieve the analytical performances stated by the manufacturer. Thus, the European Union has established some requirements to be met by an in vitro diagnostic device in order for it to be placed on the European market.

A manufacturer needs to be able to guarantee that an analysis instrument returns results within a specified analytical performance. In fact, according to the directive, the manufacturer must have a quality assurance system continuously monitoring the occurrence of any incidents which could or has put a patient at risk. Therefore, it is important to the manufacturer that not only the analysis instrument but also any accessories used in connection with the analysis instrument meet specific performance requirements. There is therefore a need for a manufacturer to control the quality of each part in a system for performing a diagnostic analysis. Thus, the manufacturer of an analysis instrument wants to have a control of the quality of accessories to be used with the analysis instrument.

Specifically, if the analysis instrument performs an analysis comprising irradiating of a sample by transmitting electromagnetic radiation through a sample carrier holding the sample, the quality of the sample carrier may greatly affect the results of the analysis. A sample carrier of poor quality may render the analysis results incorrect. In order to know the analytical performance or accuracy of the analysis results, the manufacturer needs to know the variation in quality of the sample carriers.

Thus, it is desired for the manufacturers of analysis instruments to have an increased control of the quality of sample carriers to be used in an analysis the instrument, in order to be able to guarantee the performance of the analysis instrument.

SUMMARY OF THE INVENTION

It is an object of the invention to enable a manufacturer of an analysis instrument to guarantee a correct measurement result to be used in in vitro diagnosis. It is a further object of the invention to enable the manufacturer of the analysis instrument to control the origin of sample carriers to be used in the analysis instrument.

These and other objects of the invention are achieved by means of a method according to the independent claim.

Thus, the invention provides a method for ensuring the quality of a sample carrier in connection with performing an analysis of a sample in the sample carrier in an analysis instrument for in vitro diagnosis, wherein the sample carrier is provided with a symbol for confirming the compatibility of the sample carrier with the analysis instrument. The method comprises bringing the sample carrier to an imaging position in the analysis instrument, acquiring an image of the sample carrier, and analysing the acquired image to detect the presence of a symbol for identifying the genuineness of the sample carrier. Where the sample carrier is identified as genuine, the sample carrier is approved for use in the analysis instrument and the analysis instrument is enabled to perform an analysis of the sample in the sample carrier. The analysis comprises irradiating the sample by transmitting electromagnetic radiation through the sample carrier.

The invention provides an integrated and automated control into an instrument for in vitro diagnosis so that the instrument will not work unless a genuine sample carrier is used. This implies that the manufacturer of the instrument will not be liable to guarantee correct results from the instrument regardless of the quality of the sample carrier. The manufacturer may arrange the analysis instrument to be enabled for performing an analysis only when the origin of the sample carrier is known. Thus, the manufacturer may prevent the analysis instrument to be used with a sample carrier having an unknown origin and quality. As the analysis instrument only is enabled for sample carriers that are truly genuine (e.g. manufactured by the manufacturer of the analysis instrument or under its control), the manufacturer of the analysis instrument knows the quality of the sample carrier being used in the instrument and need not worry about poor quality sample carriers causing errors in the results from the analysis instrument. Thus, the quality assurance system required by the In Vitro Diagnostics Directive may be more easily managed, since the manufacturer has control of the effects of the sample carrier on the analysis results.

Specifically, the analysis instrument may be adapted to perform a measurement based on optical response from a sample being irradiated in the analysis instrument. In such cases, the sample needs to be irradiated through the sample carrier and the optical properties of the sample carrier will affect the result. If the sample carrier has a rough surface or comprises undesired materials, the sample carrier may affect the result significantly. Since the analysis instrument only is enabled to perform analyses on samples in sample carriers of a known quality the possibility of receiving correct results is greatly improved.

The sample carrier may be placed on a carriage in the analysis instrument and the carriage may be arranged to transport the sample carrier to the imaging position and further to an analysis position if the sample carrier is identified as genuine. This implies that the sample carrier is automatically transported between the imaging and analysis positions and that there is no possibility to change the sample carrier after the sample carrier has been identified as genuine.

The analysing may comprise determining the presence of specific features in the symbol. Thus, the analysis may be arranged to merely identify some characteristics of the symbol that may easily be recognized. This makes the requirements on the image analysis rather simple to achieve.

The symbol preferably indicates the origin of the sample carrier so that the analysis instrument merely accepts sample carriers having a quality that the manufacturer of the analysis instrument may control. Thus, the symbol may be a trademark, a logotype, or a text that indicates the manufacturer of the sample carrier.

BRIEF DESCRIPTION OF THE DRAWINGS

The invention will now by way of example be described in further detail with reference to the accompanying drawings.

DETAILED DESCRIPTION OF A PRESENTLY PREFERRED EMBODIMENT

Figure 1:
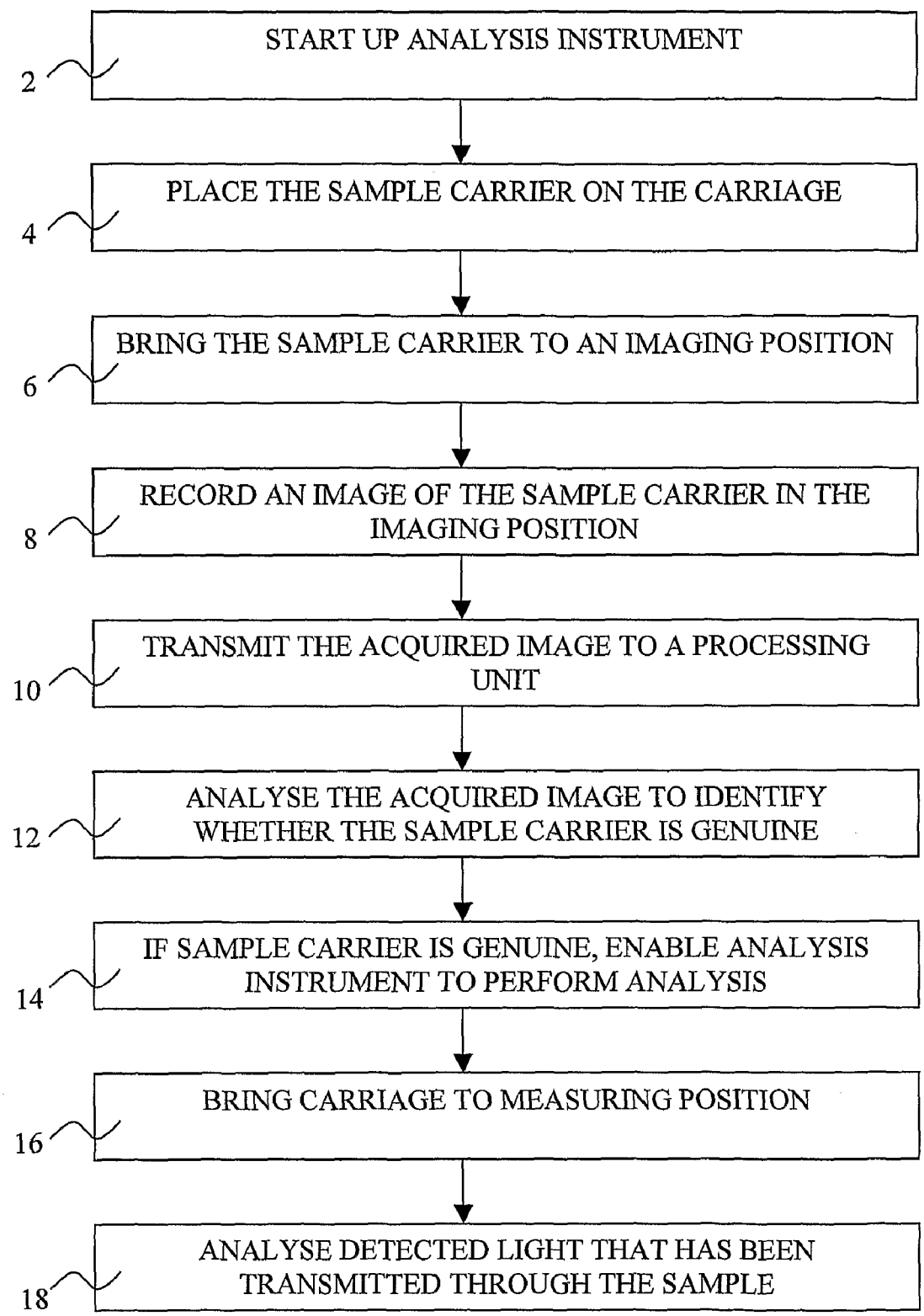
FIG. 1 is a flow chart of a method for ensuring the genuineness of a sample carrier according to one embodiment of the invention.

Referring now to FIG. 1, a method for ensuring the genuineness of a sample carrier will be described. The method is performed in conjunction with a measurement being made on a sample in the sample carrier. Thus, a user fills a sample into the sample carrier. The sample typically consists of a body liquid, such as blood. The present invention is suitable for use with a sample carrier in the form of a cuvette having a cavity for receiving a sample by capillary action. The sample may be acquired by applying the cuvette into contact with blood from a pricked finger, whereby the sample may be drawn into the sample carrier by means of capillary action.

The user then starts up an analysis instrument, step 2, which is to be used for analysing the sample. A carriage may now be projected from the analysis instrument and the user may place the sample carrier on the carriage, step 4. The analysis instrument then moves the carriage such that the sample carrier is brought to an imaging position, step 6. A digital camera in the analysis instrument records an image of the sample carrier in the imaging position, step 8. The sample carrier may be illuminated during recording of the image so that a sharper image may be obtained. The acquired image is transmitted from the digital camera to a processing unit of the analysis instrument, step 10. The processing unit analyses the acquired image, step 12. The processing unit may be programmed to detect one or more specific features in the image, which features distinguish a symbol for identifying the genuineness or origin of the sample carrier. For example, the specific features may be the contour or parts of a contour of a symbol. The symbol may e.g. be a trademark, a logotype, or text identifying the origin of the sample carrier, whereby only a specific manufacturer is allowed to use the symbol. Thus, the presence of the symbol will guarantee that the sample carrier has been produced by a certain manufacturer and that the quality of the sample carrier is within known and acceptable ranges.

If the sample carrier is identified as being genuine, the analysis instrument is enabled to perform analysis on the sample, step 14. The carriage is then brought to a measuring position, step 16. Here, the sample is irradiated by transmitting light through the sample and the sample carrier. The transmitted light is detected and the detected light is analysed in order to analyse the sample, step 18.

Figure 2:
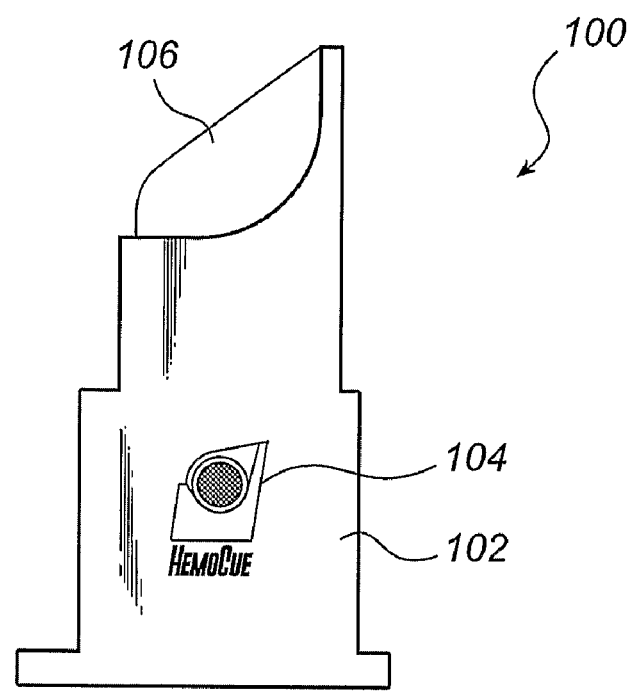
FIG. 2 is a schematic view of a sample carrier illustrating a symbol for identifying the genuineness of the sample carrier.

Referring now to FIG. 2, a sample carrier 100 having a symbol for identifying its origin will be described. The sample carrier 100 comprises a base portion 102, which will not be irradiated by light during analysis of a sample in the sample carrier 100. Thus, an operator may touch and grip the sample carrier 100 in the base portion 102 without causing any interference in analysis results. Further, the sample carrier 100 is provided with a symbol 104, which is printed on the base portion 102. Thus, the printed symbol 104 will not interfere with the light being transmitted through the sample carrier 100 during analysis of a sample. The symbol 104 is here exemplified as the trademark of HemoCue AB with a picture and the word "HemoCue". The presence of this symbol 104 may be detected by identifying by means of image analysis the outer shape of the picture and the filled circle as well as the word "HemoCue". This implies that it is not critical that the symbol 104 is printed on a very accurate position of the base portion 102. Further, the presence of the symbol 104 may be damaged to some extent. As long as the overall appearance of the symbol 104 is intact, the presence of the symbol 104 may be correctly detected. Thus, the printing of the symbol 104 on the sample carrier 100 is not required to be very accurate.

The sample carrier 100 further comprises a sample receiving cavity 106, which is arranged to receive a sample. The sample may be introduced into the sample receiving cavity 106 by means of capillary action. At least the walls of the sample receiving cavity 106 are transparent to light, such that light may be transmitted through a sample in the sample receiving cavity 106 for analysing the sample.

Figure 3:
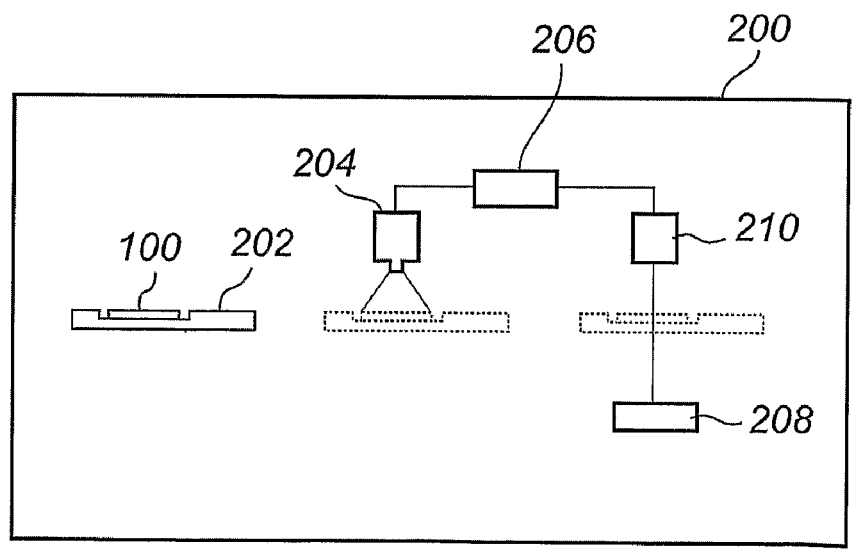
FIG. 3 is a schematic view of a set-up for analysing the genuineness of the sample carrier.

Referring now to FIG. 3, the set-up of an analysis instrument 200 will be described. The analysis instrument 200 comprises a carriage 202 that is connected to a motor and a control unit (not shown) for controlling the movement of the carriage 202. When the analysis instrument is turned on, the carriage 202 may be projected in order to receive a sample carrier 100. Alternatively, the carriage 202 may be manually projected or a lid may be opened for enabling the sample carrier 100 to be placed on the carriage 202. The control unit is arranged to move the carriage 202 to an imaging position and to a measuring position; the carriage 202 being illustrated in broken lines in these positions in FIG. 3. The analysis instrument 200 further comprises a camera 204 that is arranged to view the sample carrier 100 in the imaging position. The camera 204 is arranged to record a plan view of the sample carrier 100. The analysis instrument 200 may also comprise a light source (not shown) for illuminating the sample carrier 100 in the imaging position in order to improve the brightness of the acquired image and facilitate detection of the presence of the symbol 104 on the sample carrier 100. The camera 204 is connected to a processing unit 206, which is arranged to perform image analysis for detecting the presence of the symbol 104. The analysis instrument 200 further comprises a light source 208 and a detector 210 arranged in the measuring position. The light source 208 and the detector 210 are arranged at opposite sides of the sample carrier 100 when positioned in the measuring position. Thus, the detector 210 will detect light that has been transmitted through the sample in the sample carrier 100. The light source 208 may be one or more light emitting diodes for emitting light at one or more specific wavelengths. However, the light source 208 may be any other kind of light source that emits light in a range of wavelengths or at one or more specific wavelengths. The detector 210 may comprise a photodiode that detects the amount of light that has been transmitted. A first wavelength may thus be emitted and the photodiode may then detect the amount of transmitted light of the first wavelength. Thereafter, a second wavelength is emitted and the photodiode detects the amount of transmitted light of the second wavelength. Alternatively, the detector 210 may comprise a prism or grating or any other means for splitting light of different wavelengths, and a CCD (charge-coupled device) for detecting the amount of light of different wavelengths. The detector 210 is further connected to the processing unit 206, which may analyse the detected light in order to determine desired features of the sample. The analysis instrument 200 may further comprise a display (not shown) and the analysing unit 206 is arranged to output results of the analysis of the sample on the display.

It should be emphasized that the preferred embodiments described herein are in no way limiting and that many alternative embodiments are possible within the scope of protection defined by the appended claims.

For example, the carriage 202 may be controlled manually, in that the user manually projects the carriage 202 in order to place the sample carrier 100 on the carriage 202 and then pushes the carriage 202 into the imaging position and the measuring position. As a further alternative, the carriage 202 may be connected to a spring which brings the carriage 202 to the imaging position, when the user releases the carriage 202 from a locked, projected position. Also, any combination of manual handling and actuation by spring or motor may be used for bringing the carriage 202 between a projected position, the imaging position and the measuring position.

The invention claimed is:

1. A method for ensuring the quality of a sample carrier in connection with performing an analysis of a sample in the sample carrier in an analysis instrument for in vitro diagnosis, wherein the sample carrier is provided with a symbol for confirming the compatibility of the sample carrier with the analysis instrument, said method comprising:

placing the sample carrier on a carriage in the analysis instrument, wherein the carriage is arranged to transport the sample carrier to an imaging position and further to an analysis position if the sample carrier is identified as genuine, bringing the sample carrier to the imaging position in the analysis instrument, acquiring an image of the sample carrier, analyzing the acquired image to detect the presence of a symbol for identifying the genuineness of the sample carrier, and where the sample carrier is identified as genuine, approving the sample carrier for use in the analysis instrument and enabling the analysis instrument to perform an analysis of the sample in the sample carrier by automatically transporting the sample carrier to the analysis position, said analysis comprising irradiating the sample by transmitting electromagnetic radiation through the sample carrier.

2. The method according to claim 1, wherein the analyzing comprises determining the presence of specific features in the symbol.

3. The method according to claim 2, wherein the symbol is a trademark.

4. The method according to claim 2, wherein the symbol is a logotype.

5. The method according to claim 2, wherein the symbol is text.

6. The method according to claim 1, wherein the image is acquired by means of a camera.

7. The method according to claim 1, wherein the sample carrier is a cuvette adapted to acquire a blood sample.

8. The method according to claim 2, wherein the image is acquired by means of a camera.

9. The method according to claim 3, wherein the image is acquired by means of a camera.

10. The method according to claim 4, wherein the image is acquired by means of a camera.

11. The method according to claim 5, wherein the image is acquired by means of a camera.

12. The method according to claim 2, wherein the sample carrier is a cuvette adapted to acquire a blood sample.

13. The method according to claim 3, wherein the sample carrier is a cuvette adapted to acquire a blood sample.

14. The method according to claim 4, wherein the sample carrier is a cuvette adapted to acquire a blood sample.

15. The method according to claim 5, wherein the sample carrier is a cuvette adapted to acquire a blood sample.

* * * * *